United States Patent
Szkola et al.

(10) Patent No.: US 8,960,624 B2
(45) Date of Patent: Feb. 24, 2015

(54) MEDICAL DEVICE MOUNTING SYSTEM

(75) Inventors: Raymond E. Szkola, Batavia, IL (US); Joseph W. Jun, Geneva, IL (US); Eric Anthony Mihal, Crown Point, IN (US); Rick Paul, Kokomo, IN (US); Michael Robert Baker, Kokomo, IN (US); Terry Lee Strunk, Windfall, IN (US); Robert W. Reel, Kokomo, IN (US)

(73) Assignee: Allied Tube & Conduit Corporation, Harvey, IL (US)

( * ) Notice: Subject to any disclaimer, the term of this patent is extended or adjusted under 35 U.S.C. 154(b) by 211 days.

(21) Appl. No.: 13/352,563

(22) Filed: Jan. 18, 2012

(65) Prior Publication Data

US 2012/0248269 A1   Oct. 4, 2012

Related U.S. Application Data

(60) Provisional application No. 61/470,721, filed on Apr. 1, 2011.

(51) Int. Cl.
| | | |
|---|---|---|
| *A47F 1/00* | (2006.01) | |
| *A61B 19/04* | (2006.01) | |
| *A47F 5/08* | (2006.01) | |
| *A61B 19/02* | (2006.01) | |
| *F16M 13/02* | (2006.01) | |
| *F16M 11/22* | (2006.01) | |
| *A61G 12/00* | (2006.01) | |
| *A61B 19/00* | (2006.01) | |

(52) U.S. Cl.
CPC .................. *A61B 19/045* (2013.01); *A47F 5/08* (2013.01); *A61B 19/0256* (2013.01); *F16M 13/027* (2013.01); *A61B 19/26* (2013.01); *F16M 11/22* (2013.01); *A61G 12/004* (2013.01)

USPC ........................... 248/317; 211/113; 211/117

(58) Field of Classification Search
USPC .................... 248/317, 323; 211/117, 113, 17
See application file for complete search history.

(56) References Cited

U.S. PATENT DOCUMENTS

| | | | | |
|---|---|---|---|---|
| 2,933,198 | A | * | 4/1960 | Firestone et al. ............. 212/319 |
| 4,815,396 | A | * | 3/1989 | Gehring et al. ............... 108/149 |
| 4,840,278 | A | * | 6/1989 | Gelinas .......................... 211/18 |
| 2006/0065165 | A1 | | 3/2006 | Baez |
| 2009/0212188 | A1 | | 8/2009 | Metelski |

FOREIGN PATENT DOCUMENTS

JP          2010115287 A      5/2010

* cited by examiner

*Primary Examiner* — Amy Sterling
(74) *Attorney, Agent, or Firm* — Kacvinsky Daisak Bluni PLLC

(57) ABSTRACT

A medical device mounting system is disclosed for connecting a medical device suite to ceiling support structure. The system includes a plurality of portions connected to form a box beam structure that has high strength and high rigidity to withstand substantial bending loads associated with heavy medical device suites. The system includes a structure connection portion for engaging ceiling structure, a central mounting panel portion, and a base plate portion for engaging the medical device suite at or above the ceiling panel level. The mounting panel portion includes multiple mounting panels formed into a box beam shape. The base plate portion forms an egg-crate structure. The structure connection portion includes a plurality of tubular members that connect to longitudinal members of the mounting panel portion, and a plurality of plate portions that facilitate fixation of the assembly to ceiling structure. Other embodiments are disclosed and claimed.

19 Claims, 23 Drawing Sheets

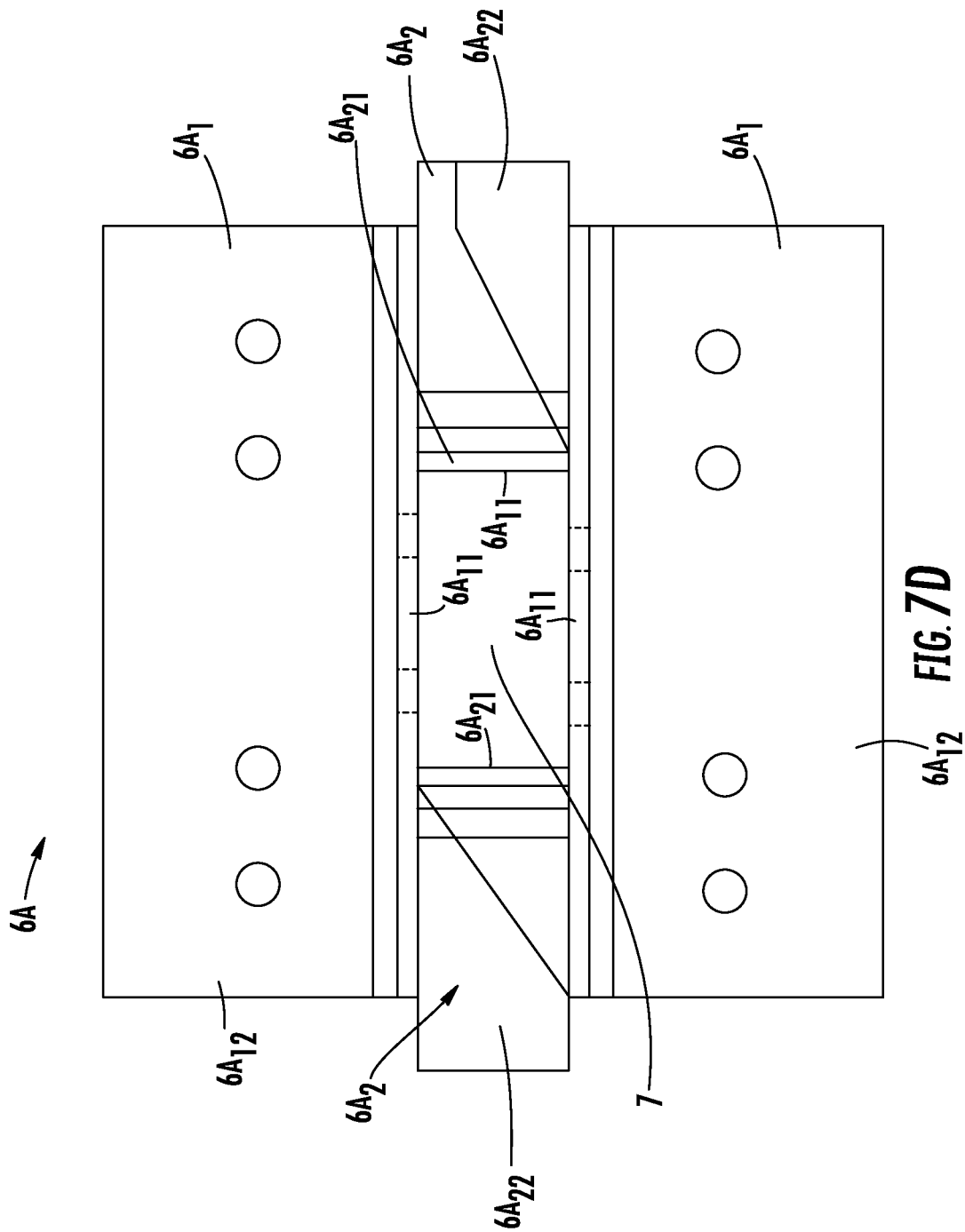

MEDICAL DEVICE MOUNTING SYSTEM

CROSS-REFERENCE TO RELATED APPLICATIONS

This is a non-provisional application of pending U.S. provisional patent application Ser. No. 61/470,721, filed Apr. 1, 2011, the entirety of which provisional application is incorporated by reference herein.

BACKGROUND OF THE INVENTION

1. Field of the Invention

Embodiments of the invention generally relate to the field of mounting systems for medical device applications, and more particularly to a highly rigid ceiling mounting system for supporting medical device suites.

2. Discussion of Related Art

Medical ceiling mounts are often used in operating rooms or intensive-care units to support various systems required for operations, intensive care or patient examination. For example, ceiling mounts may be used for the mounting of medical equipment such as medical monitors, respirators, syringe pumps, microscopes, C-arms, and the like. The advantage of such ceiling mounts is that they provide a large overhead working range and generally do not interfere with personnel in the core area of the operating theater. One major application area is intensive care medicine, in which medical devices, trays, instrument holders, etc. must be maneuverable with as much flexibility as possible in the vicinity of the patient.

In contrast to conventional floor stands, which usually are of a displaceable configuration, ceiling mounts are often fixed in position at one point (the attachment point on the ceiling, usually a ceiling console). The weight of the entire structure, and any tilting torques, are absorbed at that point.

Often multiple movable arms are attached to such ceiling mounts, with each are carrying a different device. As these arms move during operation, their movement can induce substantial moments on the mount, and thus conventional mounts must be extremely bulky to withstand the high bending loads without damage to the mount, the ceiling structure and/or the devices.

There is a need for a ceiling mount system that is compact, and that is sufficiently strong and rigid to provide desired stability for often heavy suites of medical devices that are attached thereto.

SUMMARY OF THE INVENTION

The disclosed system is a compact medical mounting assembly for use in supporting a variety of medical devices from a ceiling structure. The disclosed device is strong enough to withstand unbalanced loads associated with medical devices mounted to adjustable arms, and does not unduly impact the ceiling volume in which it is installed.

A medical device mounting system is disclosed. The mounting system may comprise a mounting panel portion having a plurality of mounting panels. Each of the plurality of mounting panels can include a plurality of longitudinal members, a plurality of horizontal members and a plurality of diagonal members. The plurality of mounting panels may be such that the mounting panel portion comprises a box beam structure. The mounting system may further comprise a base plate portion connected to a first end of the mounting panel portion. The base plate portion may include first and second sets of longitudinal members connected to form an egg-crate structure. The base plate portion may further include a plurality of plate members connected to at least one of said first and second sets of longitudinal members. The plurality of plate members can be configured to engage a medical device system. The mounting system may also include a structure connection portion connected to a second end of the mounting panel portion. The structure connection portion may include a plurality of connection sub-sections, where each of the connection sub-sections comprises a plurality of angle clips. The plurality of angle clips can be configured to engage at least one of said longitudinal members of said mounting panels.

A medical device mounting system is disclosed. The system includes a mounting panel portion comprising a plurality of mounting panels, wherein each of said plurality of mounting panels including a plurality of longitudinal members, a plurality of horizontal members, and a plurality of diagonal members. The plurality of mounting panels are arranged so that the mounting panel portion comprises a box beam structure. The system also includes a base plate portion connected to a first end of the mounting panel portion The base plate portion includes first and second sets of longitudinal members connected to form an egg-crate structure. The base plate portion further includes a plurality of plate members connected to at least one of the first and second sets of longitudinal members. The plurality of plate members are configured to engage a medical device system. The system also includes a structure connection portion connected to a second end of the mounting panel portion. The structure connection portion includes a plurality of connection sub-sections configured to engage at least one of said longitudinal members of said mounting panels.

A medical device mounting system is disclosed. The system includes a mounting panel portion comprising a plurality of mounting panels. Each of the plurality of mounting panels includes a plurality of longitudinally oriented tubular members, a plurality of horizontally oriented tubular members and a plurality of diagonally oriented tubular members. The plurality of mounting panels are arranged so that the mounting panel portion comprises a box beam structure. The system also includes a base plate portion connected to a first end of the mounting panel portion. The base plate portion comprises a plate member for engaging a medical device system, and a structure connection portion connected to a second end of the mounting panel portion. The structure connection portion includes a plurality of connection sub-sections, where each of said connection sub-sections is configured to engage at least one of said longitudinal members of said mounting panels. Each of the connection sub-sections is also configured to engage a ceiling support structure for connecting the medical device mounting system to a ceiling structure.

A medical device mounting system is disclosed. The system includes a mounting panel portion comprising a plurality of mounting panels. Each of the plurality of mounting panels includes a plurality of tubular members arranged such that the mounting panel portion comprises a box beam structure. The system includes a base plate portion connected to a first end of the mounting panel portion. The base plate portion comprises first and second sets of longitudinal members connected to form an egg-crate structure. The base plate portion also includes a plurality of plate members configured to engage a medical device system. The system further comprises a structure connection portion connected to a second end of the mounting panel portion, where the structure connection portion configured to engage at least one of said longitudinal members of said mounting panels.

BRIEF DESCRIPTION OF THE DRAWINGS

The accompanying drawing illustrates an exemplary embodiment of the disclosed device so far devised for the practical application of the principles thereof, and in which:

FIGS. 7A-D are top plan, side and end views, respectively, of a first embodiment of a structure connection portion of the medical device mounting system of FIG. 1;

DESCRIPTION OF EMBODIMENTS

Figure 1:
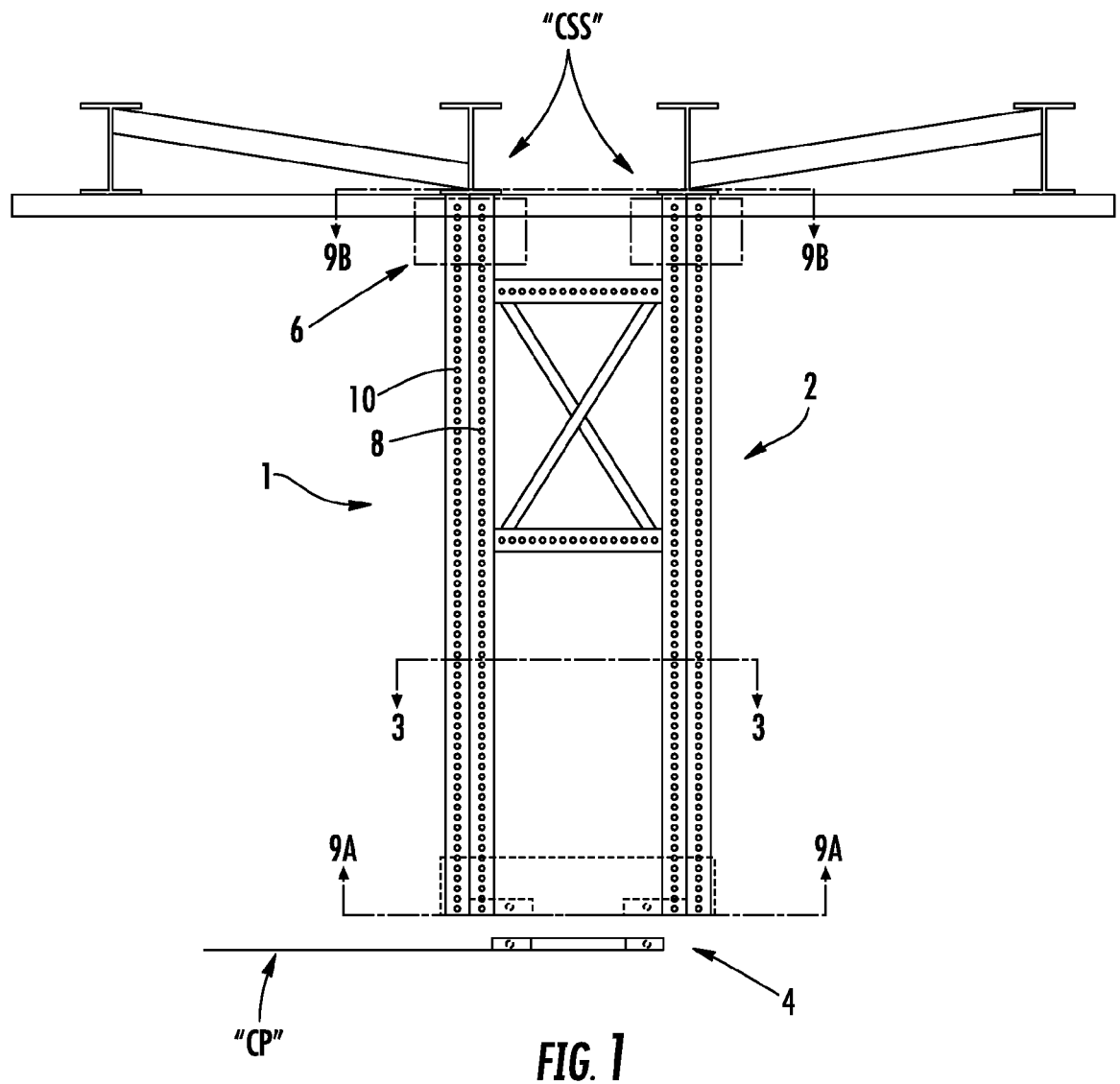
FIG. 1 is a first side view of the disclosed medical device mounting system attached to ceiling structure.
Figure 2:
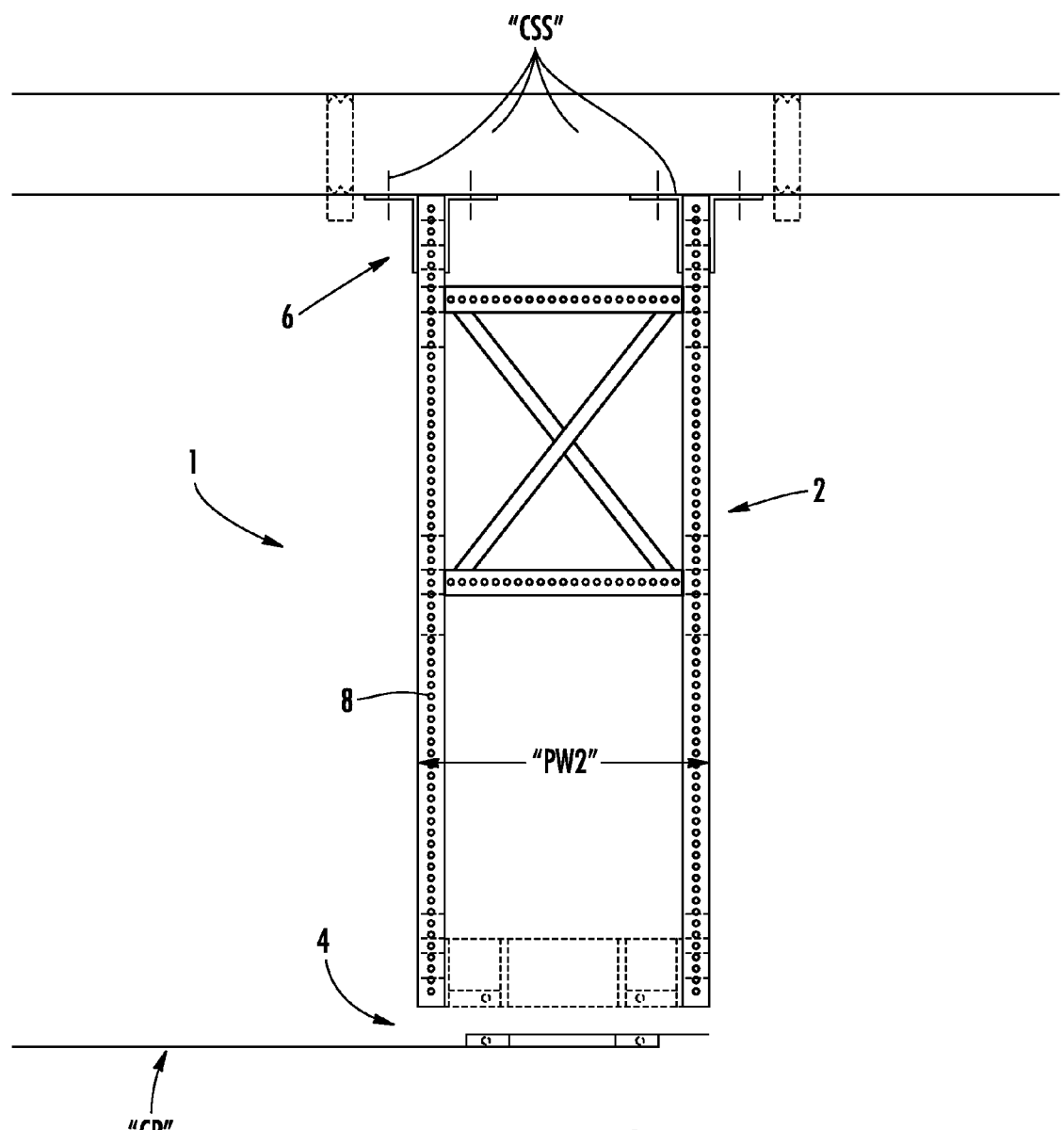
FIG. 2 is a second side view of the medical device mounting system of FIG. 1, rotated 90-degrees.
Figure 3:
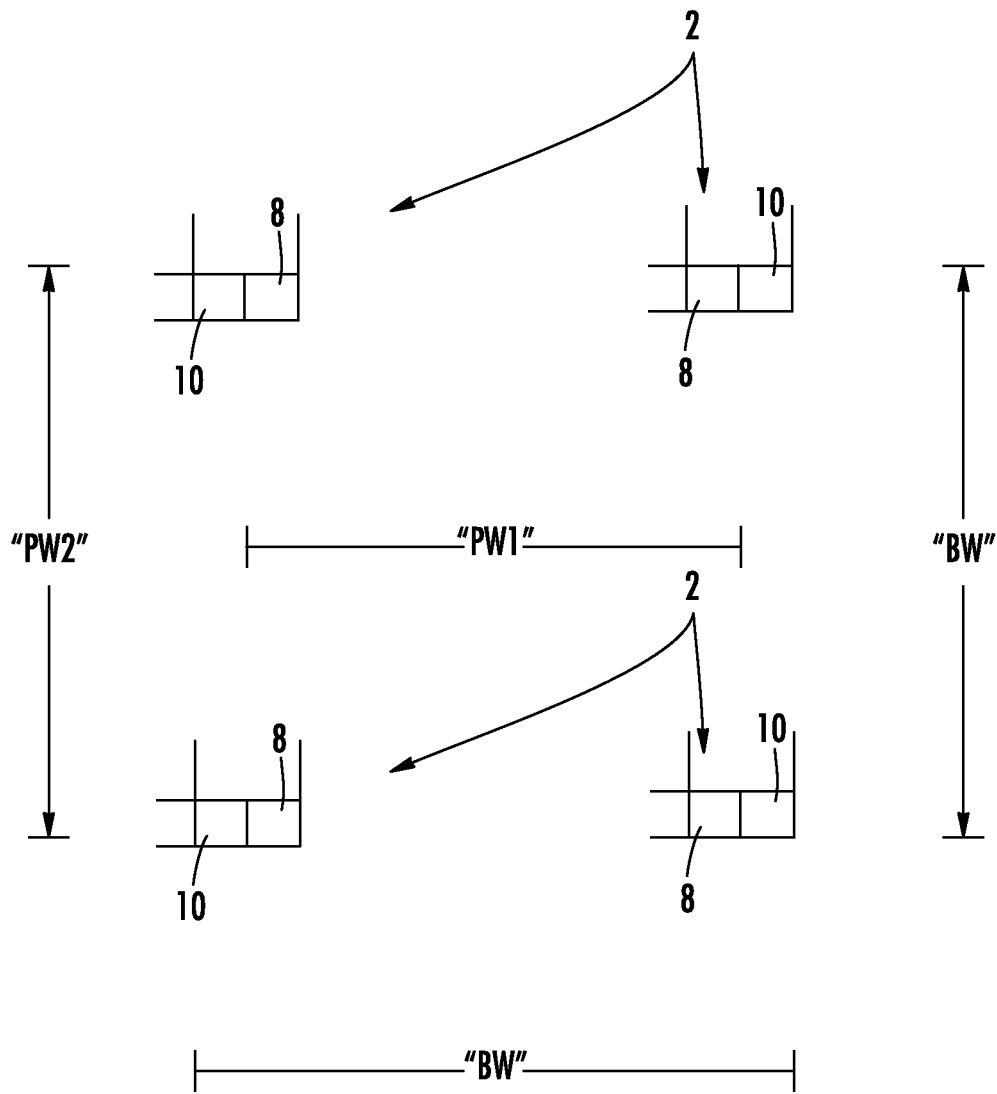
FIG. 3 is a cross-section view of the medical device mounting system of FIG. 1, taken along line 3-3.

Referring to FIGS. 1-3, a medical device mounting system 1 is illustrated in a position engaged with exemplary ceiling support structure "CSS". The medical device mounting system 1 generally includes a mounting panel portion 2, a base plate portion 4, and a structure connection portion 6. The structure connection portion 6 is configured to attach to ceiling structure located above the ceiling plane "CP." The base plate portion 4 is configured to attach to one or more medical device suspension devices, such as suspension arms and the like. In use, the medical device mounting system will be disposed above the ceiling such that only the attached medical device system(s) will protrude below the ceiling itself.

The mounting panel portion 2 of the system 1 includes a plurality of longitudinal structural members configured into a box-like arrangement, which provides the mounting system 1 its substantial stiffness. This box-beam arrangement is formed from first and second pairs of mounting panels 8, 10. A face of one of the first mounting panels 8 is shown in FIG. 1, while a face of one of the second mounting panels 10 is shown in FIG. 2.

FIGS. 4A-4E illustrate features of the first mounting panel 8, which includes a pair of spaced-apart longitudinal structural members 8A, a pair of spaced-apart horizontal structural members 8B, and a pair of diagonal structural members 8C. As shown, the longitudinal structural members 8A have first and second ends $8A_1$, $8A_2$. The horizontal structural members 8B also have first and second ends $8B_1$, $8B_2$. The horizontal structural members are spaced apart by a distance "HD," and are connected to the longitudinal structural members 8A such that their first ends $8B_1$ are connected to a first one of the longitudinal members and their second ends $8B_2$ are connected to a second one of the longitudinal members.

Figure 4A:
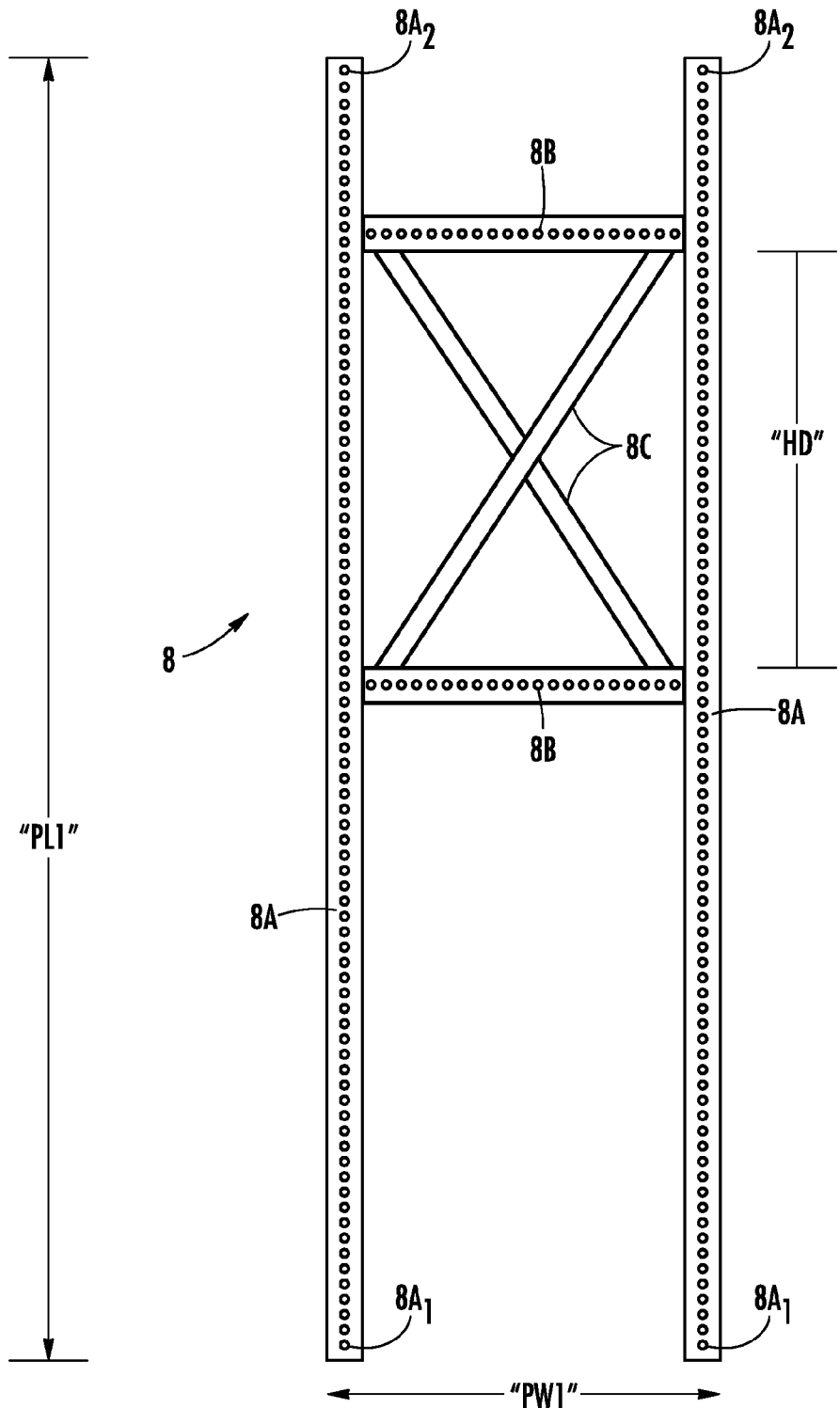
FIGS. 4A-4E are side views of a first mounting panel of the medical device mounting system of FIG. 1.
Figure 4B:
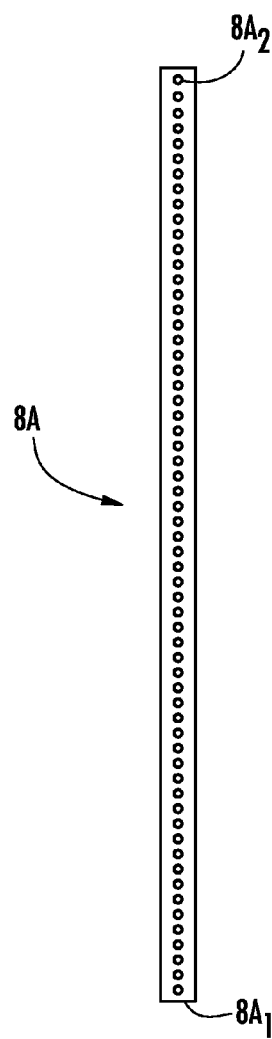
Figure 4C:
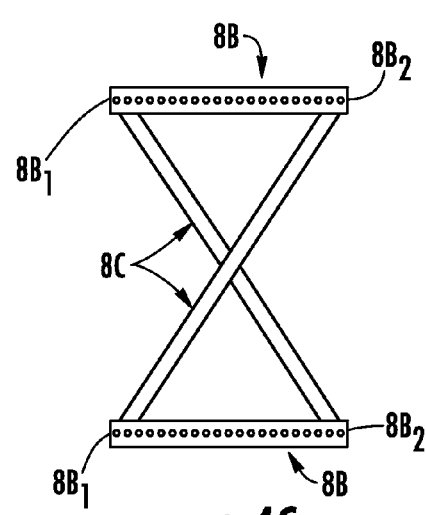
Figure 4D:
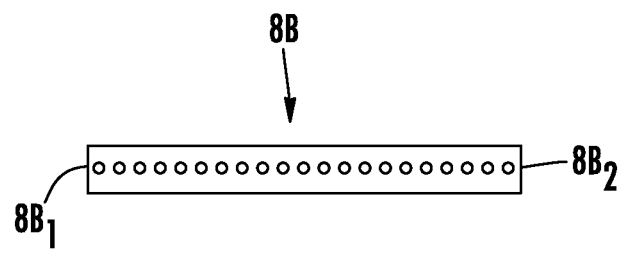
Figure 4E:
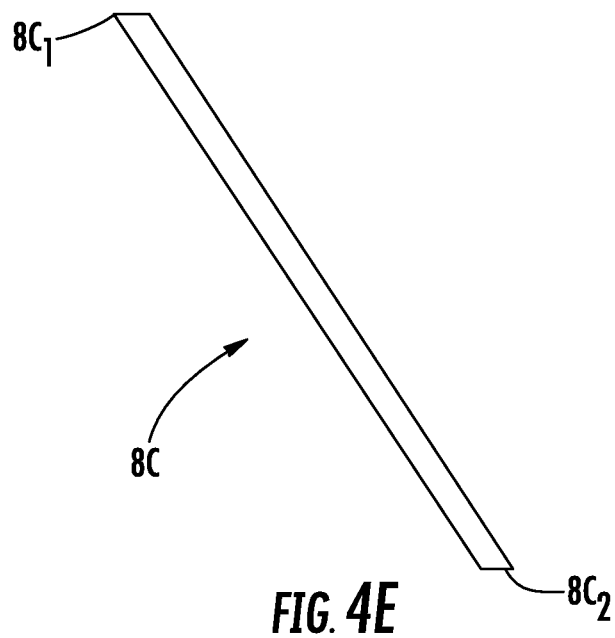

Each of the diagonal structural members 8C has first and second ends $8C_1$, $8C_2$, which are positioned to engage the horizontal and longitudinal structural members 8A, 8B to form an "X" arrangement between the pair of horizontal structural members 8B. The first end $8C_1$ of each diagonal member connects to a first end $8B_1$ of one of the pair of horizontal structural members 8B, while the second end $8C_2$ of each diagonal member connects to a second end $8B_2$ of the other of the pair of horizontal structural members. In some embodiments, this "X" arrangement (or "racking arrangement") may be placed closer to the top end of the structure than the bottom end. For shorter mounting systems, the racking arrangement may be optional. For longer mounting systems, the racking arrangement may be duplicated one or more times along the length of the mounting system (see, e.g., FIGS. 11A, 11B). The resulting "racking" arrangement of horizontal and diagonal structural members is shown in FIG. 4C. This configuration provides enhanced racking strength to the first mounting panel 8.

The longitudinal and horizontal structural members 8A, 8B are sized to provide the first mounting panel 8 with a desired length "PL1," and a desired width "PW1." The length "PL1" and width "PW1" may be adjusted depending upon the requirements (e.g., load, stiffness) of a particular medical device being supported, and/or by the physical limitations of the area above the ceiling.

Referring now to FIGS. 5A-5E features of the second mounting panel 10 will be described. As can be seen, the second mounting panel 10 is generally configured in the same manner as the first mounting panel 8. Thus, the second mounting panel 10 includes a pair of spaced-apart longitudinal structural members 10A, a pair of spaced-apart horizontal structural members 10B, and a pair of diagonal structural members 10C. The longitudinal structural members 10A have first and second ends $10A_1$, $10A_2$, the horizontal structural members 10B have first and second ends $10B_1$, $10B_2$, and the diagonal structural members 10C have first and second ends $10C_1$, $10C_2$.

Figure 5A:
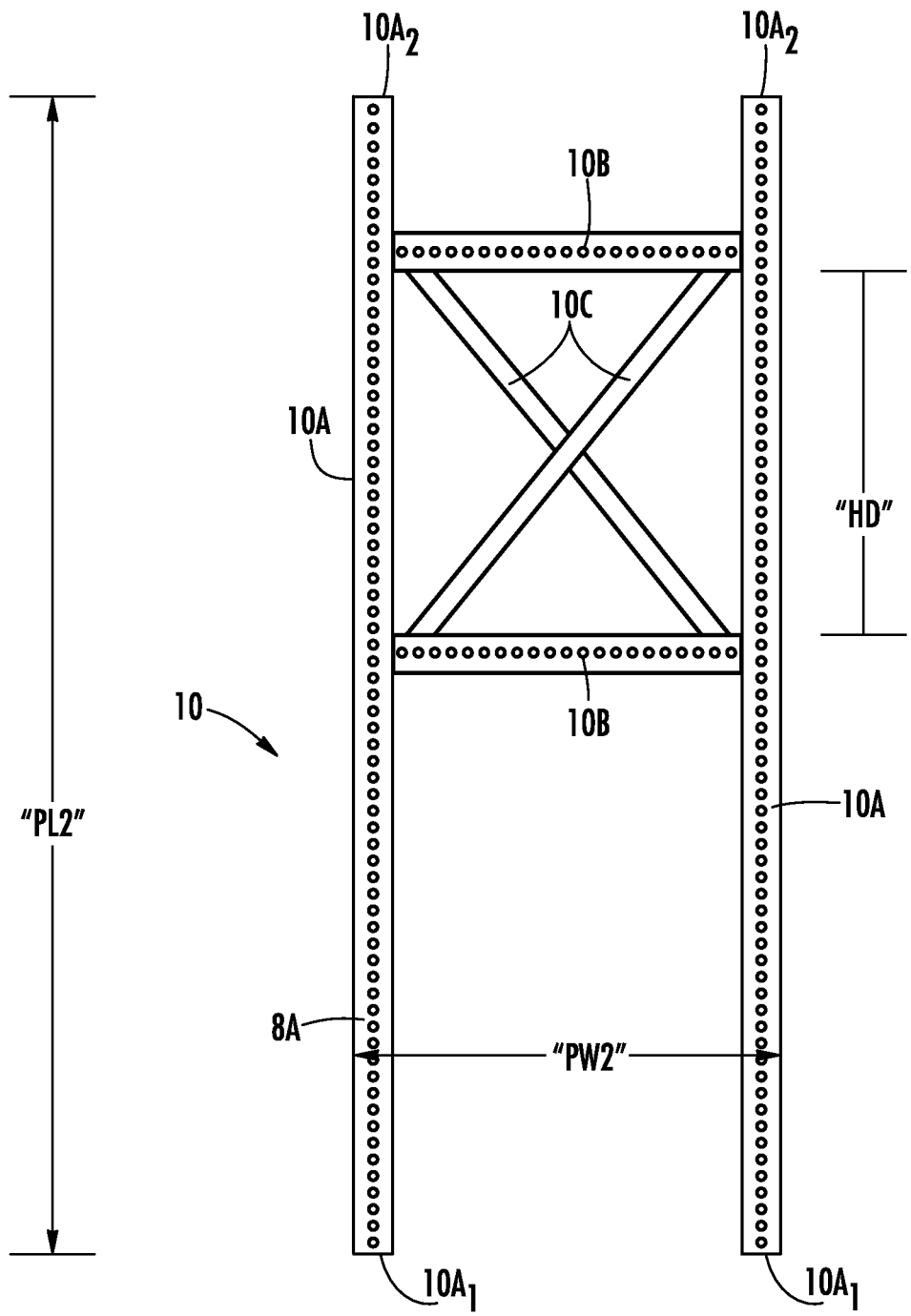
FIGS. 5A-5E are side views of a second mounting panel of the medical device mounting system of FIG. 1.
Figure 5B:
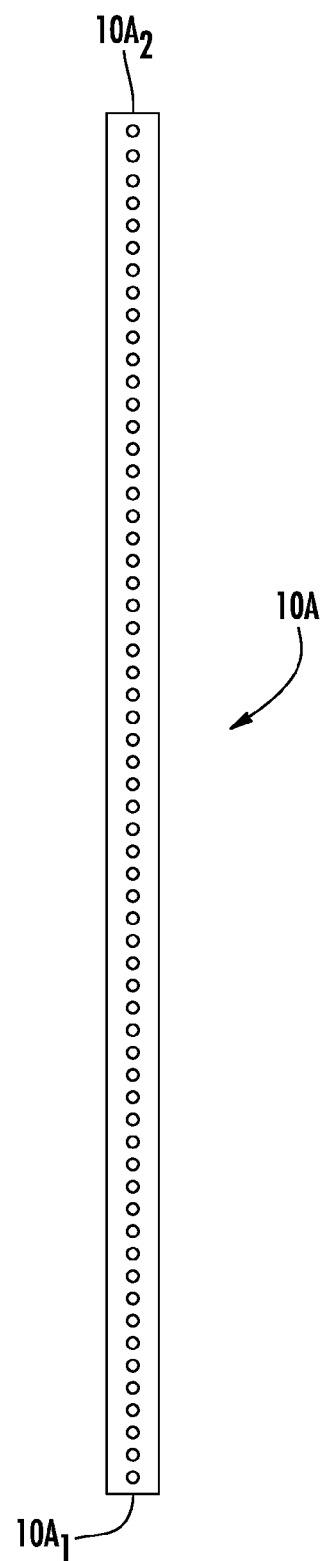
Figure 5C:
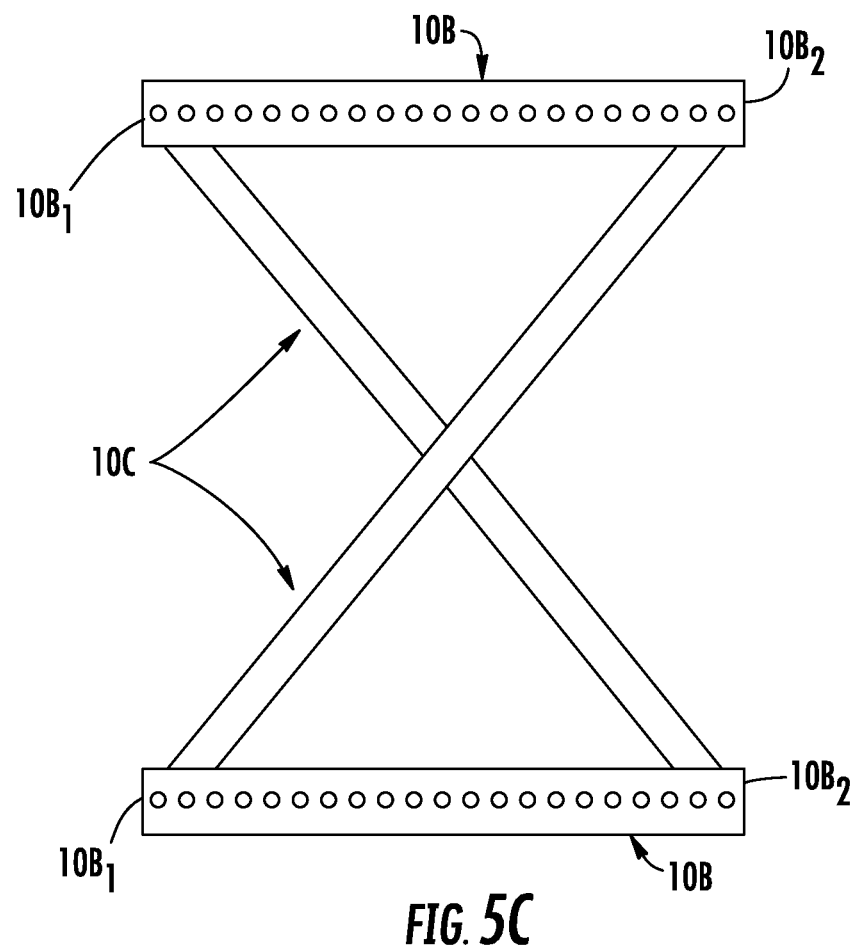
Figure 5D:
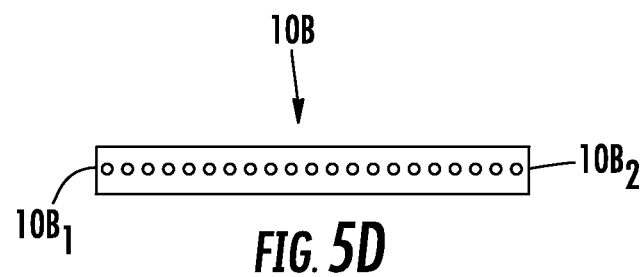
Figure 5E:
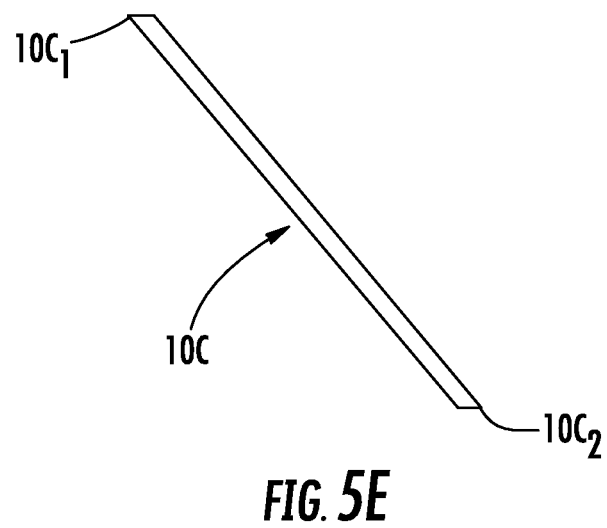

The horizontal structural members are spaced apart by a distance "HD," and are connected to the longitudinal structural members 10A such that their first ends $10B_1$ are connected to a first one of the longitudinal members 10A and their second ends $10B_2$ are connected to a second one of the longitudinal members 10A. The diagonal structural members 10C are positioned to engage the horizontal and longitudinal structural members 10A, 10B to form an "X" arrangement. Thus, the first end $10C_1$ of each diagonal member connects to a first end $10B_1$ of one of the pair of horizontal structural members 10B and the second end $10C_2$ of each diagonal member connects to a second end $10B_2$ of the other of the pair of horizontal structural members. The resulting "racking" arrangement of horizontal and diagonal structural members 10B, 10C is shown in FIG. 5C. As with the first panel, the illustrated configuration provides enhanced racking strength to the second mounting panel 10.

The longitudinal and horizontal structural members 10A, 10B are sized to provide the second mounting panel 10 with a desired length "PL2," and a desired width "PW2." As can be seen, "PL2" is substantially the same as "PL1," while "PW2" is slightly larger than "PW1." Referring back to FIG. 3, it can be seen that the first mounting panels 8 are connected to the second mounting panels such that the resulting square box beam formed by the pairs of panels 8, 10 has a box width "BW" that is equal to the width of the second panel "PW2".

In the illustrated embodiment, the longitudinal and horizontal structural members 8A, 8B; 10A, 10B are 2-inch×2-inch square steel tubular members, while the diagonal structural members 8C, 10C are ½ inch flat steel members. The longitudinal structural members 8A, 10A may be made from at least 13 gauge material, while the horizontal and diagonal structural members 8B, 10B, 8C, 10C may be made from at least 14 gauge material. The structural members may be welded together at the previously described connection points. Alternatively, some of the structural members may be connected together using appropriately sized fasteners, such as rivets and/or nut/bolt combinations.

To provide additional stiffness to the individual longitudinal members 8A, 10A at desired locations, additional angle members may be welded or fastened to exterior portions of the longitudinal members.

Figure 6A:
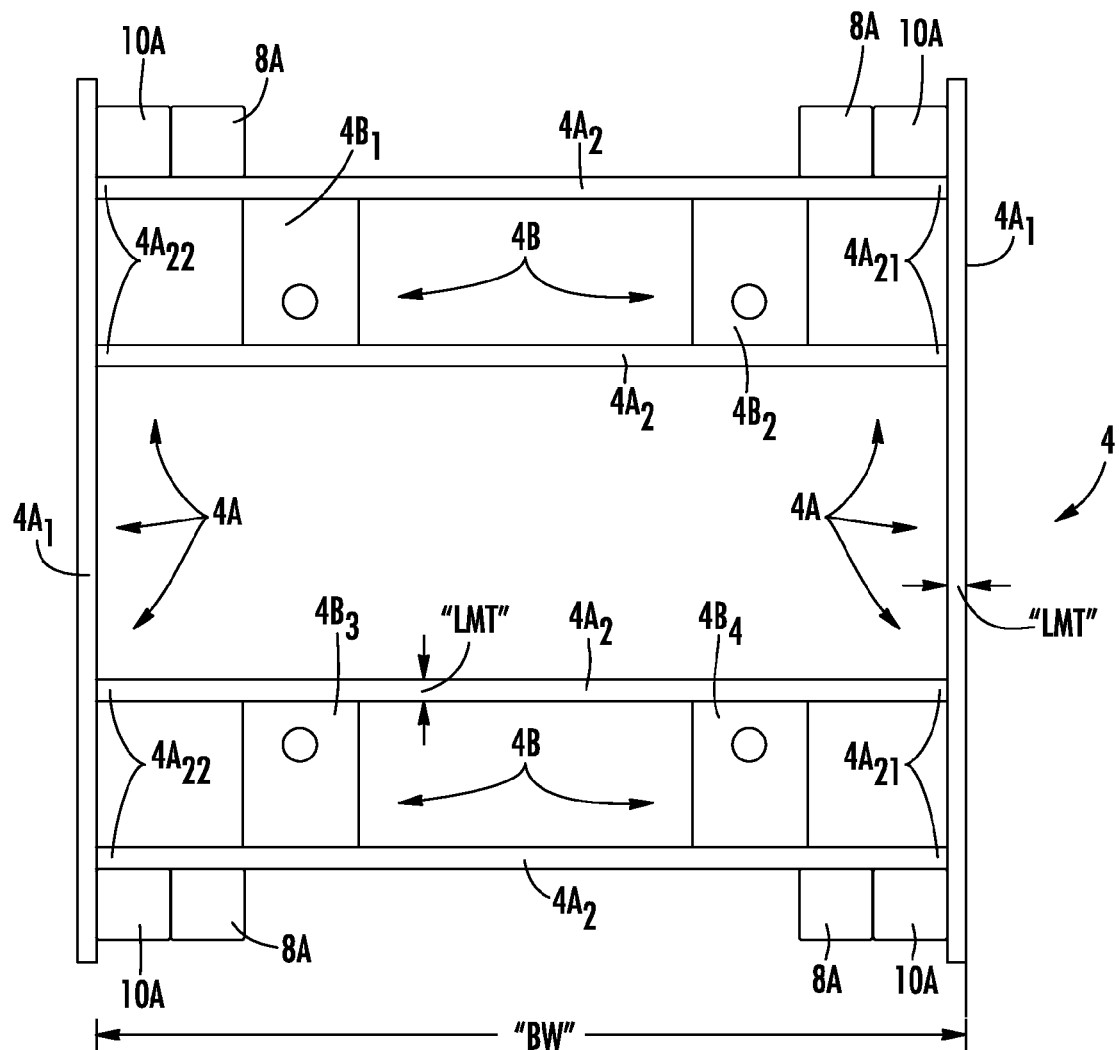
FIGS. 6A and 6B are top plan and end views, respectively, of a base plate of the medical device mounting system of FIG. 1.
Figure 6B:
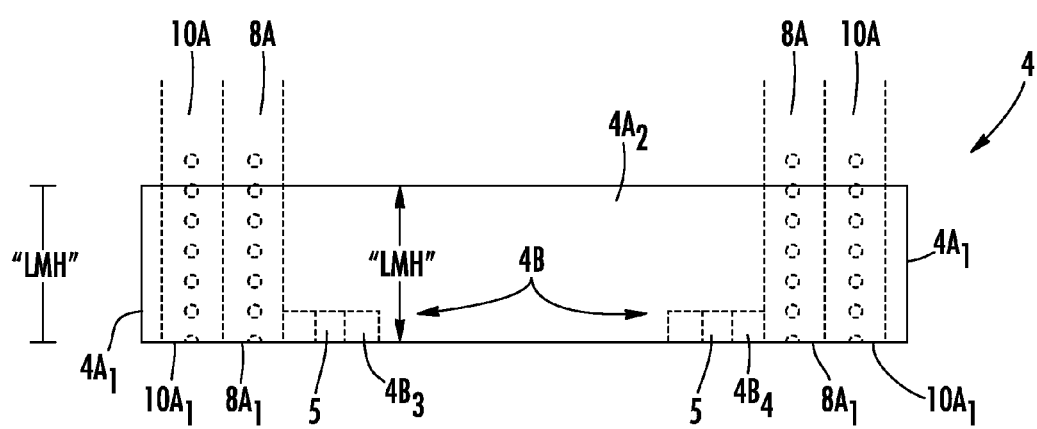

Referring now to FIGS. 6A and 6B, the base plate portion 4 of the system 1 will be described. As previously noted, the base plate portion 4 provides the interface connection between the disclosed system 1 and a medical device system, such as a suspension arm.

In the illustrated embodiment, the base plate portion 4 comprises a plurality of longitudinal members oriented to form a substantially square box structure that is engageable with the longitudinal structural members 8A, 10A of the first and second mounting panels 8, 10. The base plate portion 4 generally includes a structural portion 4A and a medical device engagement portion 4B.

The structural portion 4A includes first and second sets of longitudinal members $4A_1$, $4A_2$. In the illustrated embodiment, the first set of longitudinal members $4A_1$ comprise first and second members positioned parallel with each other and spaced apart by a distance "BW." Distance "BW" may be substantially the same as the distance "PW2" (FIG. 5A) to allow the structural portion 4A to engage the longitudinal members 8A, 10A of the first and second mounting panels 8, 10.

The second set of longitudinal members $4A_2$ comprise first, second, third and fourth members positioned parallel to each other, and perpendicular to the first set of longitudinal members $4A_1$. Thus, first ends $4A_{21}$ of the second set of longitudinal members $4A_2$ are connected to one member of the first set $4A_1$, while second ends $4A_{22}$ of the second set $4A_2$ are connected to the other member of the first set $4A_1$.

As can be seen, the individual longitudinal members each have a height "LMH" that is substantially greater than their thickness "LMT." The resulting arrangement approximates an egg-crate structure having substantial stiffness in all three planes.

The medical device engagement portion 4B includes individual plates $4B_1$-$4B_4$ connected between adjacent ones of the second set of longitudinal members $4A_2$. Each of the individual plates $4B_1$-$4B_4$ includes a hole 5 configured to receive fasteners for attaching the base plate portion 4 to a medical device system. It will be appreciated that the size, arrangement, number of individual plates, and number of fastener holes may be varied depending upon the particular application.

The base plate portion 4 engages the mounting panel portion 2 near the first ends $8A_1$, $10A_1$ of the longitudinal structural members 8A, 10A of the first and second mounting panels 8, 10. In the illustrated embodiment, the longitudinal structural members 8A, 10A engage the first and second sets of longitudinal members $4A_1$, $4A_2$ where the outside sets of members $4A_1$, $4A_2$ intersect. The base plate portion 4 may be connected to the mounting panel portion 2 at these points via welding, or through the use of appropriately sized fasteners.

In the illustrated embodiment, the long longitudinal members $4A_1$, $4A_2$ are ½-inch thick steel plate members (i.e., "LMT" is about ½-inch), having a height "LMH" of about 5-inches. The plates $4B_1$-$4B_4$ are 1-inch thick steel plate members. These members may be welded together at the previously described connection points. Alternatively, one or more of these members may be connected together using appropriately sized fasteners.

Referring now to FIGS. 7A-7D, a first embodiment of the structure connection portion 6 will be described in greater detail. The structure connection portion 6, as previously noted, is configured to connect the mounting panel portion 2 to ceiling structure (CSS) located above the ceiling plane "CP" (see FIG. 1).

As such, the structure connection portion 6 comprises a plurality of connection sub-sections 6A, each configured to engage one of the four corners of the mounting panel portion 2. The connection sub-sections 6A are also each configured to engage the ceiling support structure ("CSS") (see also FIG. 1).

Figure 7A:
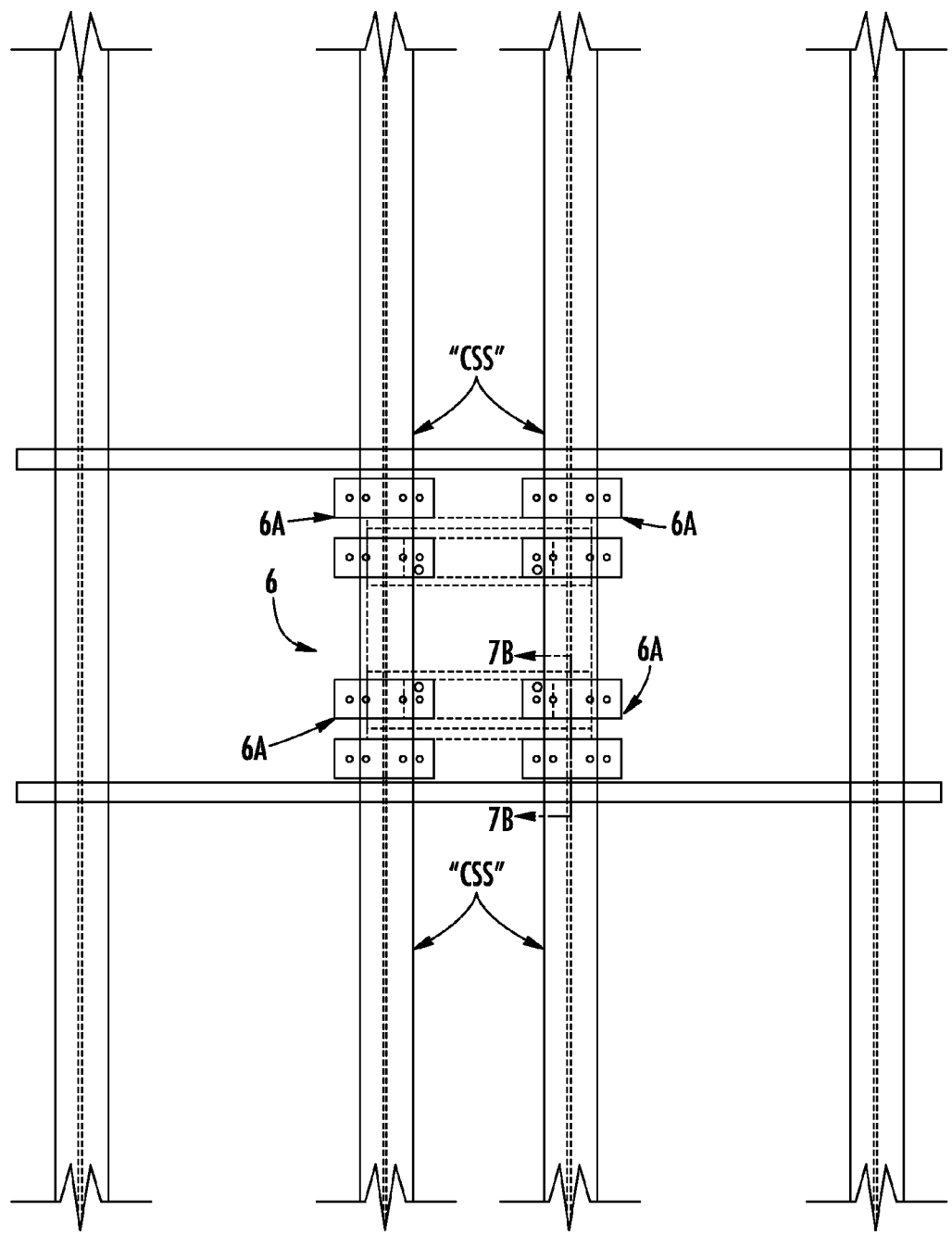
Figure 7B:
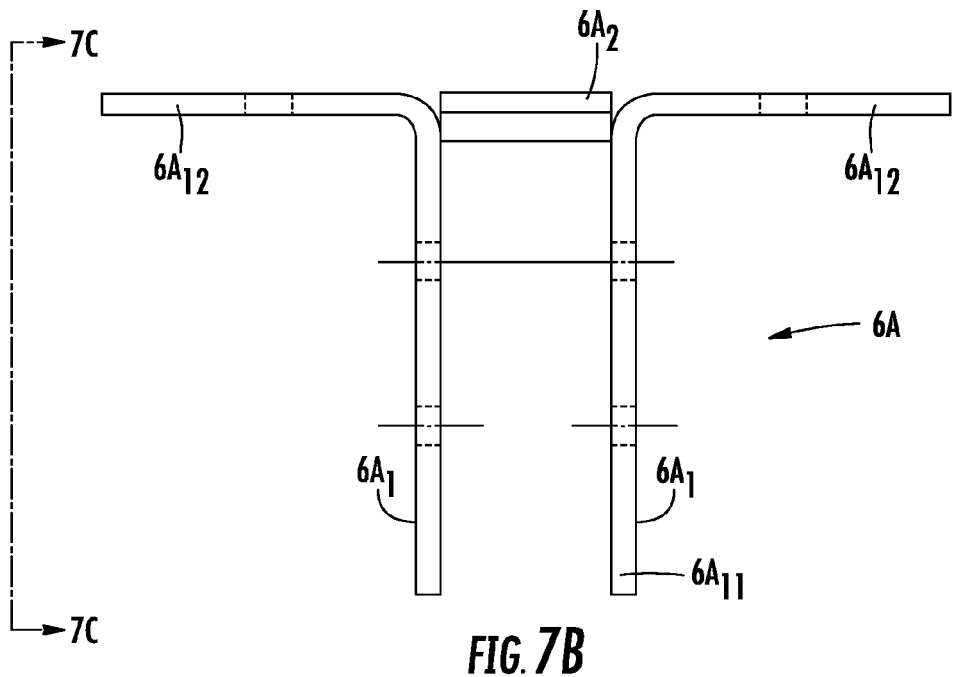
Figure 7C:
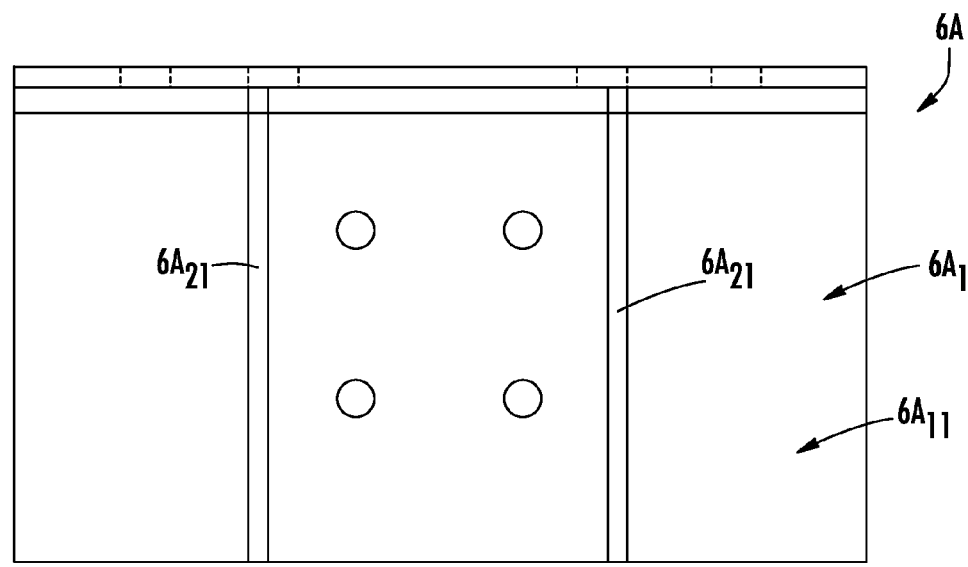
Figure 8A:
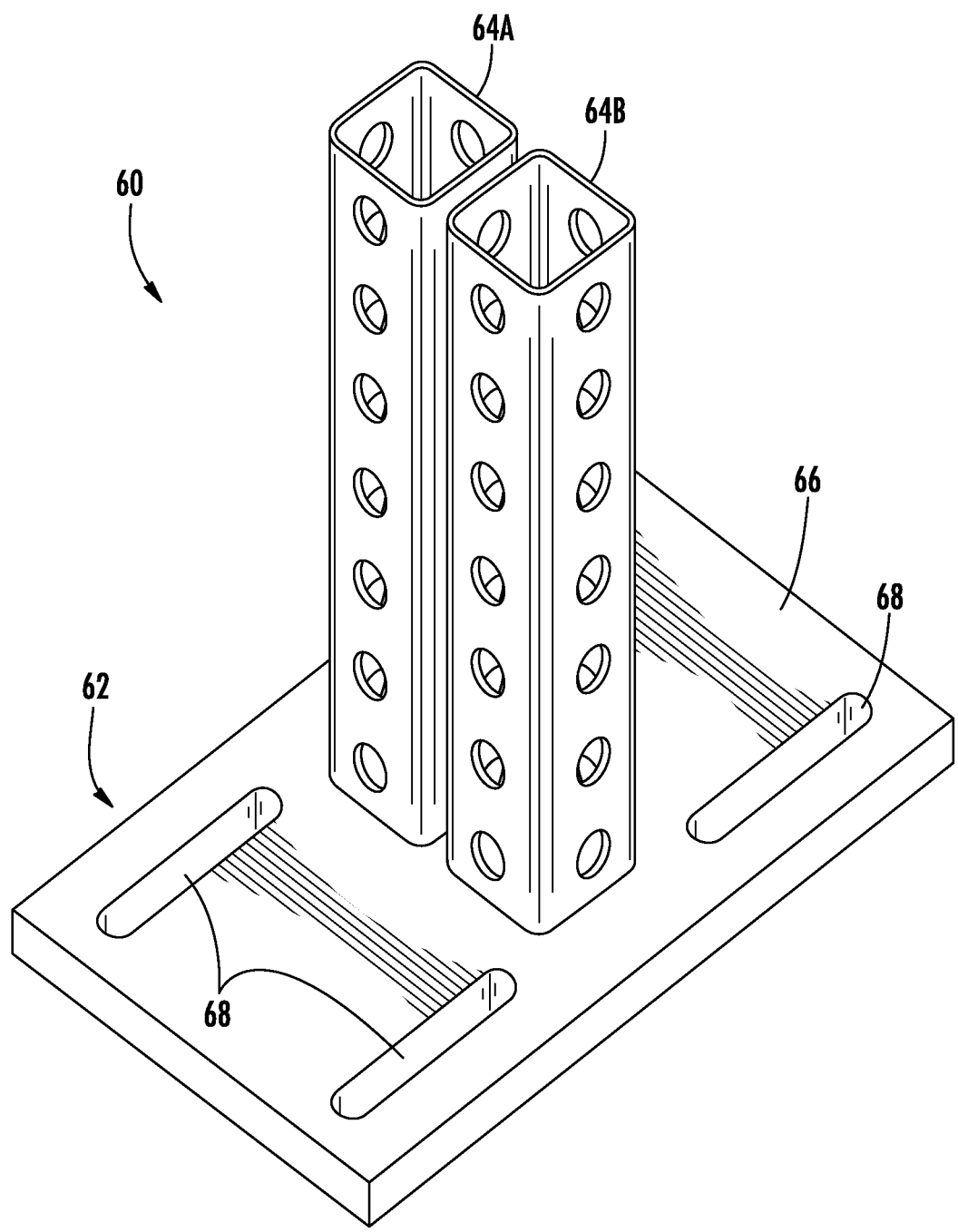
FIGS. 8A, 8B, 8C and 8D are isometric, front, side and top plan views of a second embodiment of a structure connection portion of the medical device mounting system of FIG. 1.
Figure 8B:
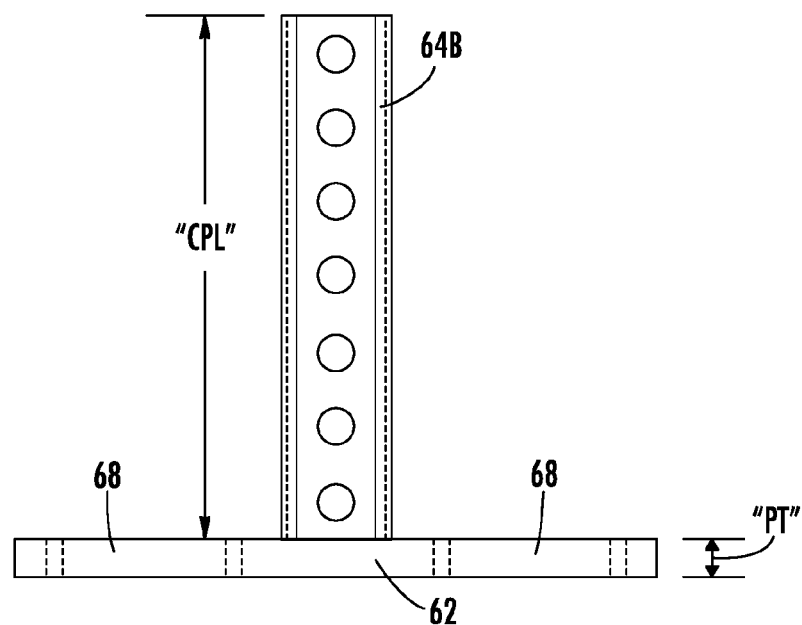
Figure 8C:
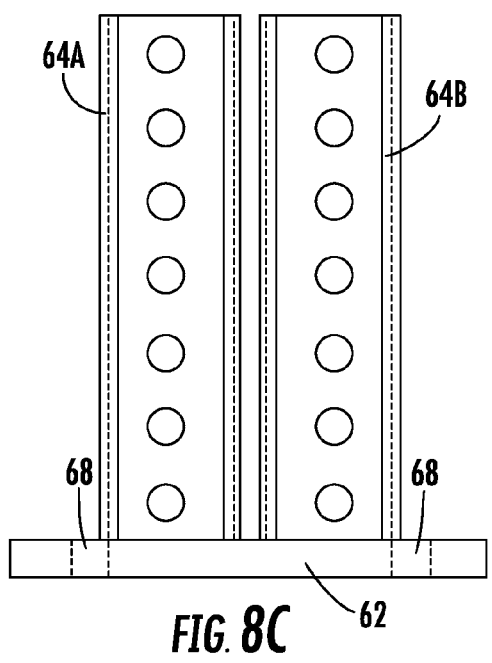
Figure 8D:
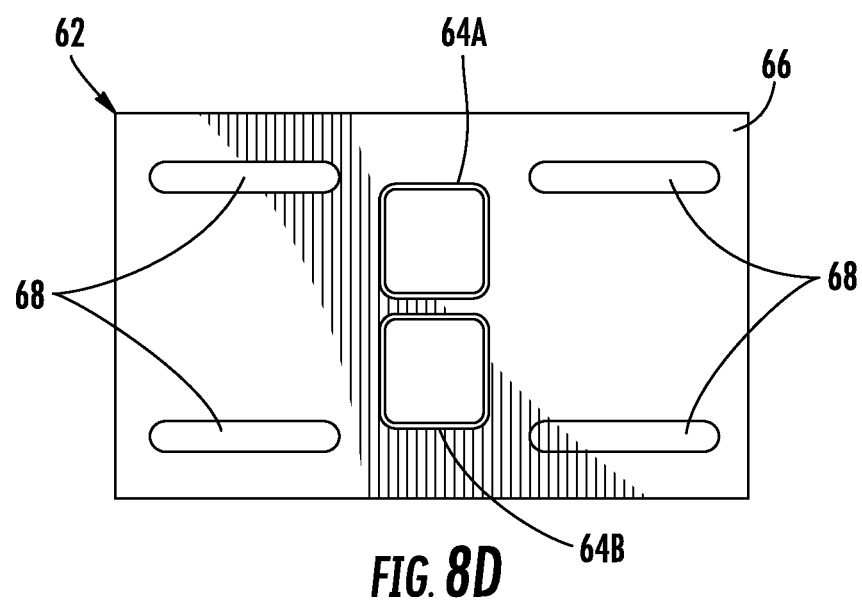

FIG. 7A shows a plan view of a first embodiment of the structure connection portion 6, taken from above the ceiling support structure (CSS), showing the structure connection portion connected to the CSS. FIG. 7B is a cross-section view of a single connection sub-section 6A taken along line 7B-7B of FIG. 7A. FIG. 7C is a side view of the connection sub-section 6A of FIG. 7B, while FIG. 7D is a top plan view of the same connection sub-section 6A.

As can be seen, the connection sub-sections 6A include first and second pairs of opposing structural angle clips $6A_1$, $6A_2$. The first angle clips $6A_1$ are positioned with respect to each other so that their vertical legs $6A_{11}$ are parallel to each other, and their horizontal legs $6A_{12}$ point away from each other. The second angle clips $6A_2$ are similarly positioned with respect to each other so that their vertical legs $6A_{21}$ are parallel to each other, and their horizontal legs $6A_{22}$ diverge from each other.

The second pairs of angle clips $6A_2$ are sandwiched between the first pairs of angle clips $6A_1$ so that a vertically-oriented enclosure 7 is formed by the respective vertical legs $6A_{11}$, $6A_{21}$ of the clips. This vertically-oriented enclosure 7 is sized to receive respective pairs of longitudinal structural members 8A, 10A, of the mounting panel portion 2. Thus arranged, each of the connection sub-sections 6A is configured to engage one of the four corners of the mounting panel portion 2.

Each of the angle clips $6A_1$, $6A_2$ may have one or more holes disposed in the horizontal and/or vertical legs $6A_{11}$, $6A_{12}$, $6A_{21}$, $6A_{22}$ to receive suitably-sized fasteners for connecting the structure connection portion 6 to the ceiling support structure (CSS) and/or the mounting panel portion 2. Alternatively, or in addition, portions of the angle clips may be welded to the CSS and/or the mounting panel portion 2.

In one embodiment, the angle clips are made from ¼-inch thick steel, and the individual pairs of clips $6A_1$, $6A_2$ are welded together to form the individual connection sub-sections 6A. It will be appreciated that other sizes, material types, and connection types can also be used as desired.

Referring now to FIGS. 8A-8D, a second embodiment of the structure connection portion will be described in greater detail. The structure connection portion 60 of FIGS. 8A-8D may function similarly to the structure connection portion 6 of FIGS. 7A-7D. Thus, the structure connection portion 60 is configured to connect the mounting panel portion 2 to ceiling structure (CSS) located above the ceiling plane "CP" in the manner shown in FIG. 1.

As can be seen, the structure connection portion 60 provides a simplified arrangement as compared to the multiple angle-clip arrangement of structure connection portion 6. Thus, the structure connection portion 60 comprises a plate portion 62 and first and second tubular members 64A, 64B oriented substantially perpendicular to an upper surface 66 of the plate portion. The first and second tubular members 64A, 64B may have a connection portion length "CPL" to provide a desired length of engagement between the structure connection portion and the mounting panel portion 2. In one embodiment, the connection portion length "CPL" is about 7-inches.

The first and second tubular members 64A, 64B may be square steel tubular members. In one embodiment, the first and second tubular members 64A, 64B are 1¾-inch square tubular members made from steel of at least 12 gauge. It will be appreciated that other tubular shapes (circular, triangular), gauges, and materials can also be used provided the resulting structure connection portion 60 provides a desired strength and stiffness. In one embodiment, the first and second tubular members 64A, 64B may be welded to the plate portion 62.

The plate portion 62 may include a plurality of holes 68 for receiving fasteners to enable the structure connection portion 60 to be connected to the ceiling support structure "CSS." In the illustrated embodiment the holes 68 as elongated so they can receive fasteners in any of a variety of positions along the hole, thus providing a degree of flexibility in engaging the structure connection portion 60 to the ceiling support structure CSS. It will be appreciated, however, that the holes could be circular, and also that greater numbers of holes 68 could be used. In one exemplary embodiment, the plate portion 62 is a steel plate having a plate thickness "PT" of about ½-inch.

Figure 9A:
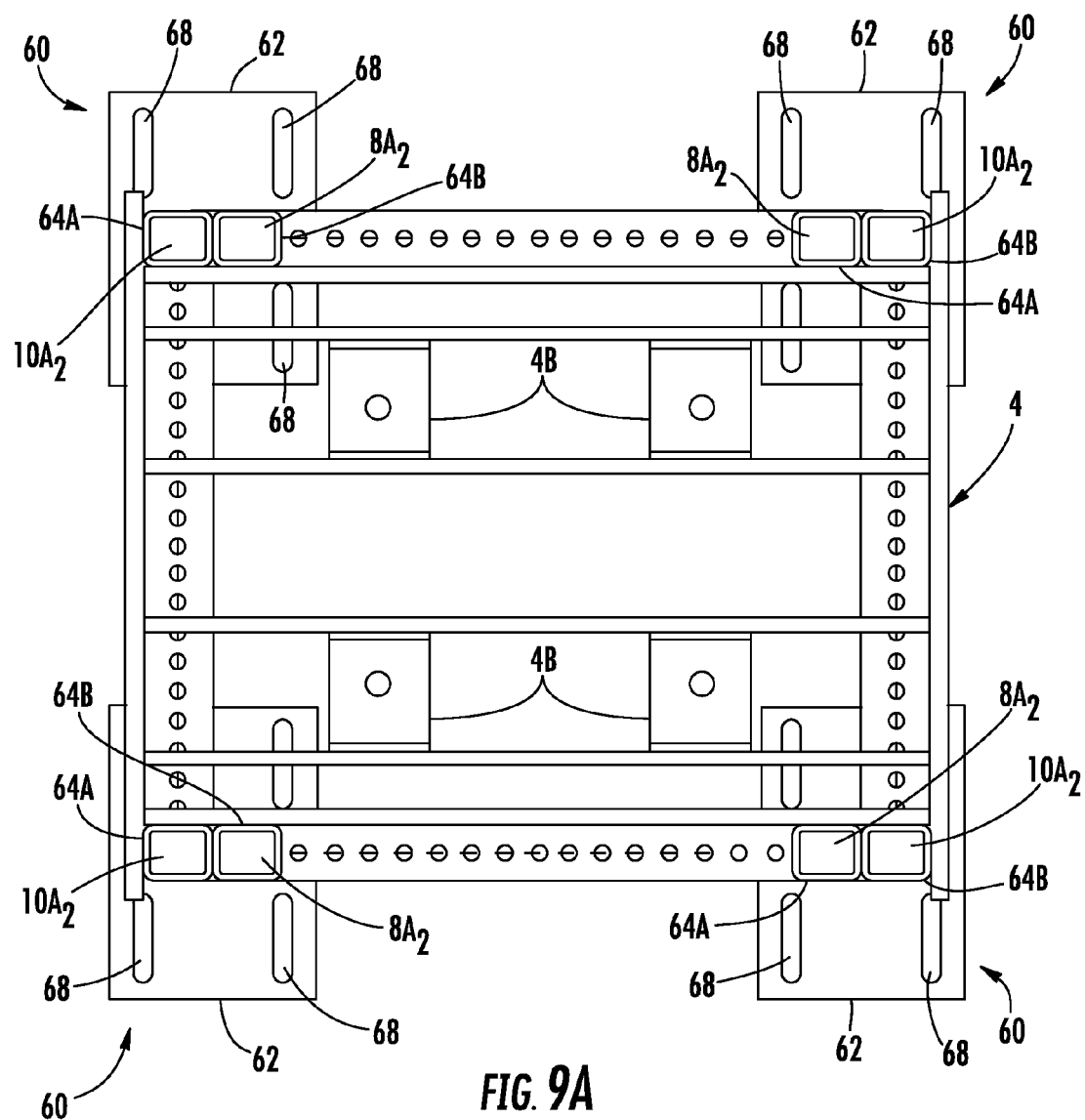
FIGS. 9A and 9B are top and bottom plan views, taken along lines 9A-9A and 9B-9B respectively, of the medical device mounting system of FIG. 1 including the second embodiment of the structure connection portion of FIGS. 8A-D.
Figure 9B:
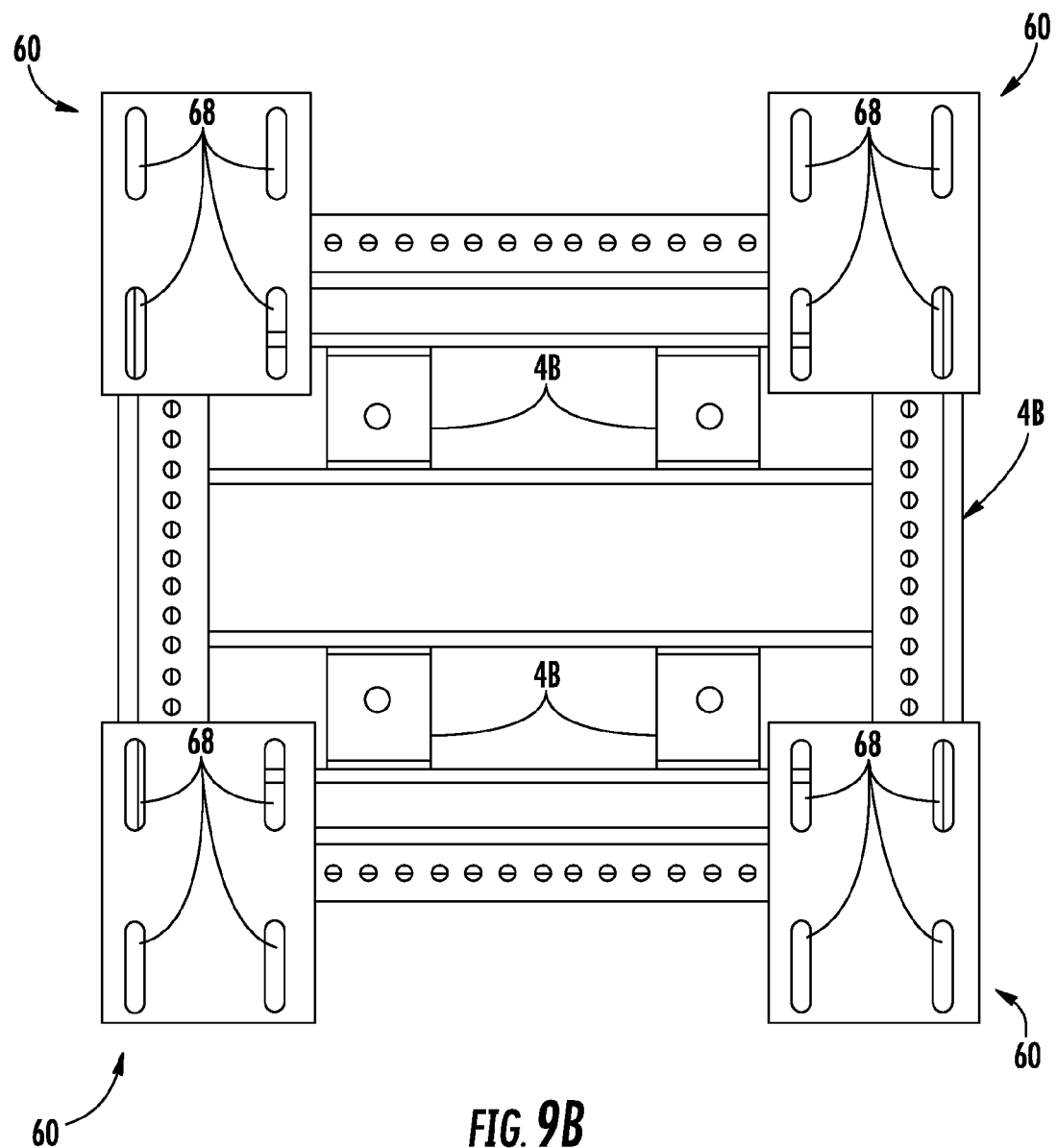

In use, the first and second tubular members 64A, 64B can engage one of the four corners of the mounting panel portion 2, while the plate portion 62 can engage the ceiling support structure (CSS) to thereby connect the mounting panel portion 2 to the ceiling in a manner similar to that shown in FIG. 1. FIGS. 9A and 9B show the structure connection portion 62 engaged with four corners of the mounting panel portion 2. Namely, the first and second tubular members 64A, 64B engage the second ends $8A_2$, $10A_2$ of longitudinal structural members 8, 10 of the mounting panel portion 2. In one embodiment, the first and second tubular members 64A, 64B are sized and configured to be received within the second ends $8A_2$, $10A_2$ of longitudinal structural members 8, 10. It will be appreciated, however, that this could be reversed such that the first and second tubular members 64A, 64B can be sized and configured to be received within the second ends $8A_2$, $10A_2$ of longitudinal structural members 8, 10.

The first and second tubular members 64A, 64B may have one or more holes disposed along the length thereof to receive suitably-sized fasteners for connecting the structure connection portion 60 to the second ends $8A_2$, $10A_2$ of longitudinal structural members 8, 10. Alternatively, or in addition, portions of the first and second tubular members 64A, 64B may be welded to the second ends $8A_2$, $10A_2$ of longitudinal structural members 8, 10.

Figure 10A:
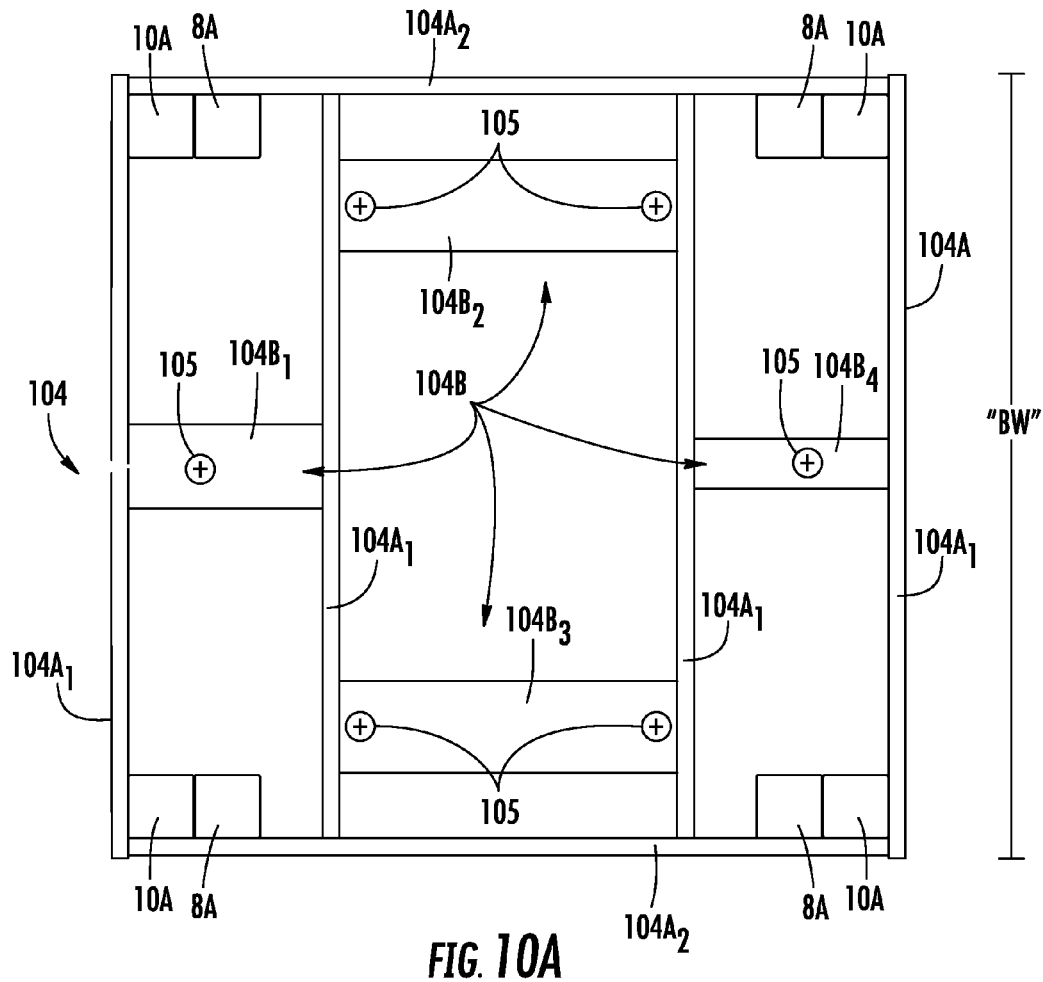
FIGS. 10A and 10B are top plan and side views, respectively, of an alternative base plate of the medical device mounting system of FIG. 1.
Figure 10B:
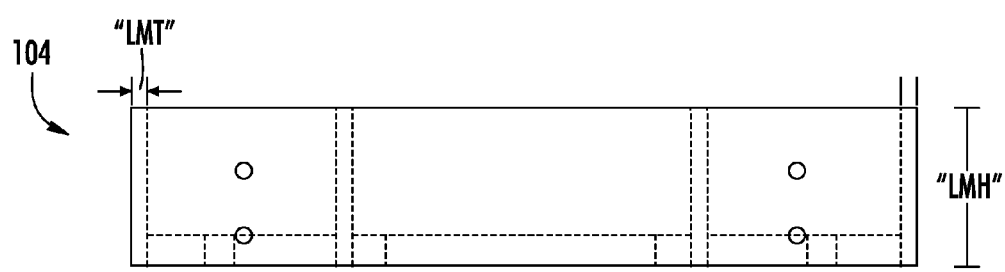

FIGS. 10A and 10B show an alternative base plate portion 104, which may be used for mounting two or more medical device systems. The base plate portion 104 is similar to the base plate portion 4 described in relation to FIGS. 6A and 6B. Thus, the base plate portion 104 comprises a plurality of longitudinal members oriented to form a substantially square box structure that is engageable at its inside corners with the longitudinal structural members 8A, 10A of the first and second mounting panels 8, 10. The base plate portion 104 generally includes a structural portion 104A and a medical device engagement portion 104B.

The structural portion 104A includes first and second sets of longitudinal members $104A_1$, $104A_2$. In the illustrated embodiment, the first set of longitudinal members $104A_1$ comprise first, second, third and fourth members positioned parallel with each other. The second set of longitudinal members $104A_2$ comprise first and second members spaced apart by a distance "BW" that is substantially the same as the distance "PW2" (FIG. 5A). The first and second sets of longitudinal members $104A_2$, $104A_2$ are connected to form an egg-crate arrangement as previously described. As with the previous embodiment, the individual longitudinal members each have a height "LMH" that is substantially greater than their thickness "LMT." The resulting egg-crate arrangement provides the structure with substantial stiffness in all three planes.

The medical device engagement portion 104B includes individual plates $104B_1$-$104B_4$ connected between adjacent ones of the second set of longitudinal members 104A1. Each of the individual plates $104B_1$-$104B_4$ includes one or more holes 105 configured to receive fasteners for attaching the base plate portion 104 to a medical device system. It will be appreciated that the size, arrangement, and number of individual plates may be varied depending upon the particular application.

The base plate portion 104 engages the mounting panel portion 2 near the first ends $8A_1$, $10A_1$ of the longitudinal structural members 8A, 10A of the first and second mounting panels 8, 10. In the illustrated embodiment, the longitudinal structural members 8A, 10A engage the first and second sets of longitudinal members $104A_1$, $104A_2$ where the outside sets of members $104A_1$, $104A_2$ intersect. The base plate portion 104 may be connected to the mounting panel portion 2 at these points via welding, or through the use of appropriately sized fasteners.

In the illustrated embodiment, the long longitudinal members $104A_1$, $104A_2$ are ½-inch thick steel plate members (i.e., "LMT" is about ½-inch), having a height "LMH" of about 5-inches. The plates $104B_1$-$104B_4$ are 1-inch thick steel plate members. These members may be welded together at the previously described connection points. Alternatively, one or more of these members may be connected together using appropriately sized fasteners.

Although the disclosed system has been described in relation to particular material types, sizes and connection methods, it will be appreciated that these materials, sizes, materials and connection methods are only examples, and are not intended to limit the scope of the disclosed structure. It is contemplated that other sizes, shapes, gauges and materials can be used to form the structural members, depending upon the specific final operating conditions of the medical device mounting system.

For example, in one alternative embodiment, the disclosed system may include a single post/tube on each corner of the mount as compared to the double-post/tube configuration shown in the figures. Such an arrangement can be modified by size or thickness to support required loads. In addition, individual dimensions of the resulting structure, as well as size and dimensions of the individual structural elements, may be based on individual configuration of the ceiling structure to which the system will be mounted.

Figure 11A:
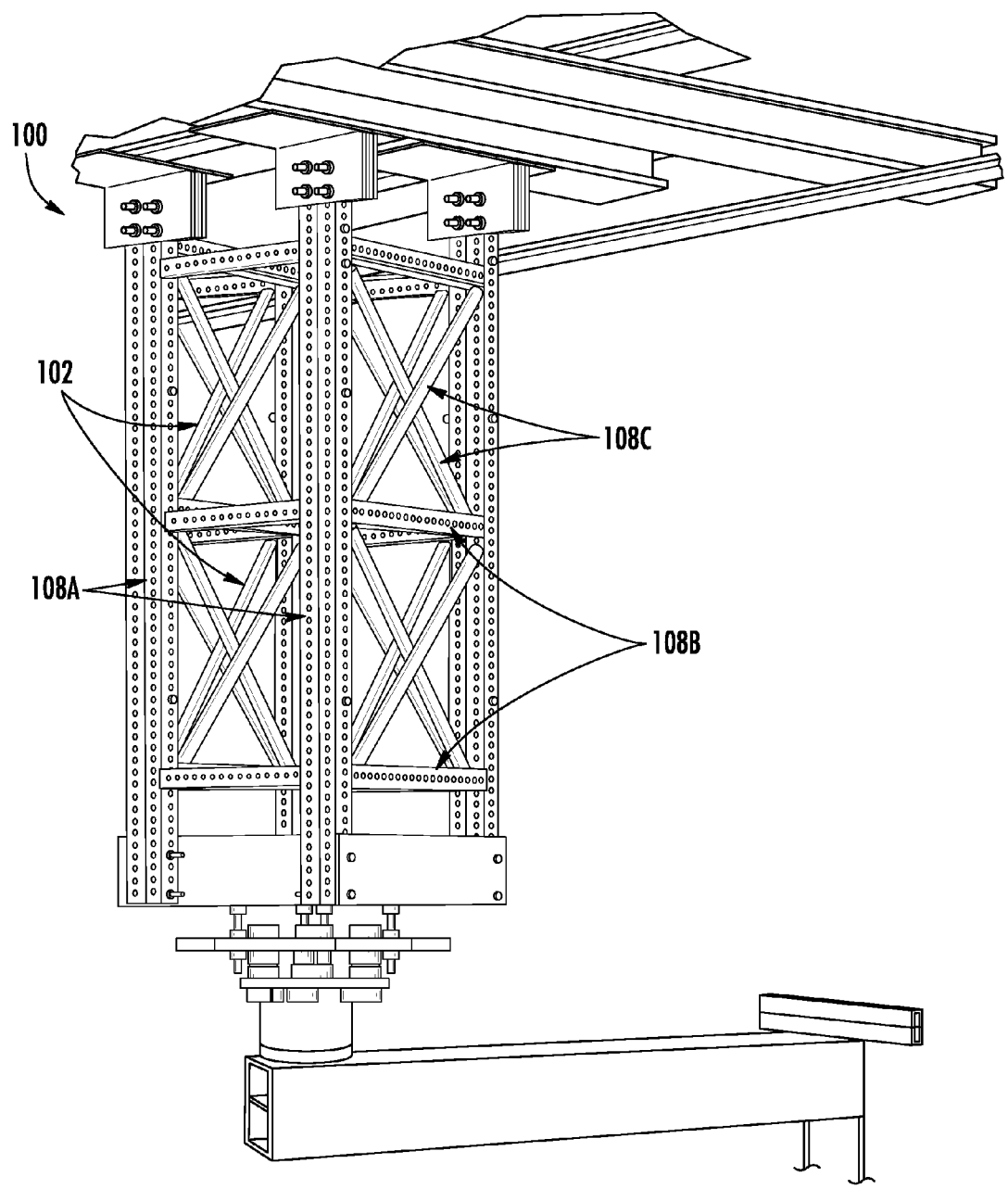
FIGS. 11A and 11B are isometric views of an alternative embodiment of the disclosed medical device mounting system.
Figure 11B:
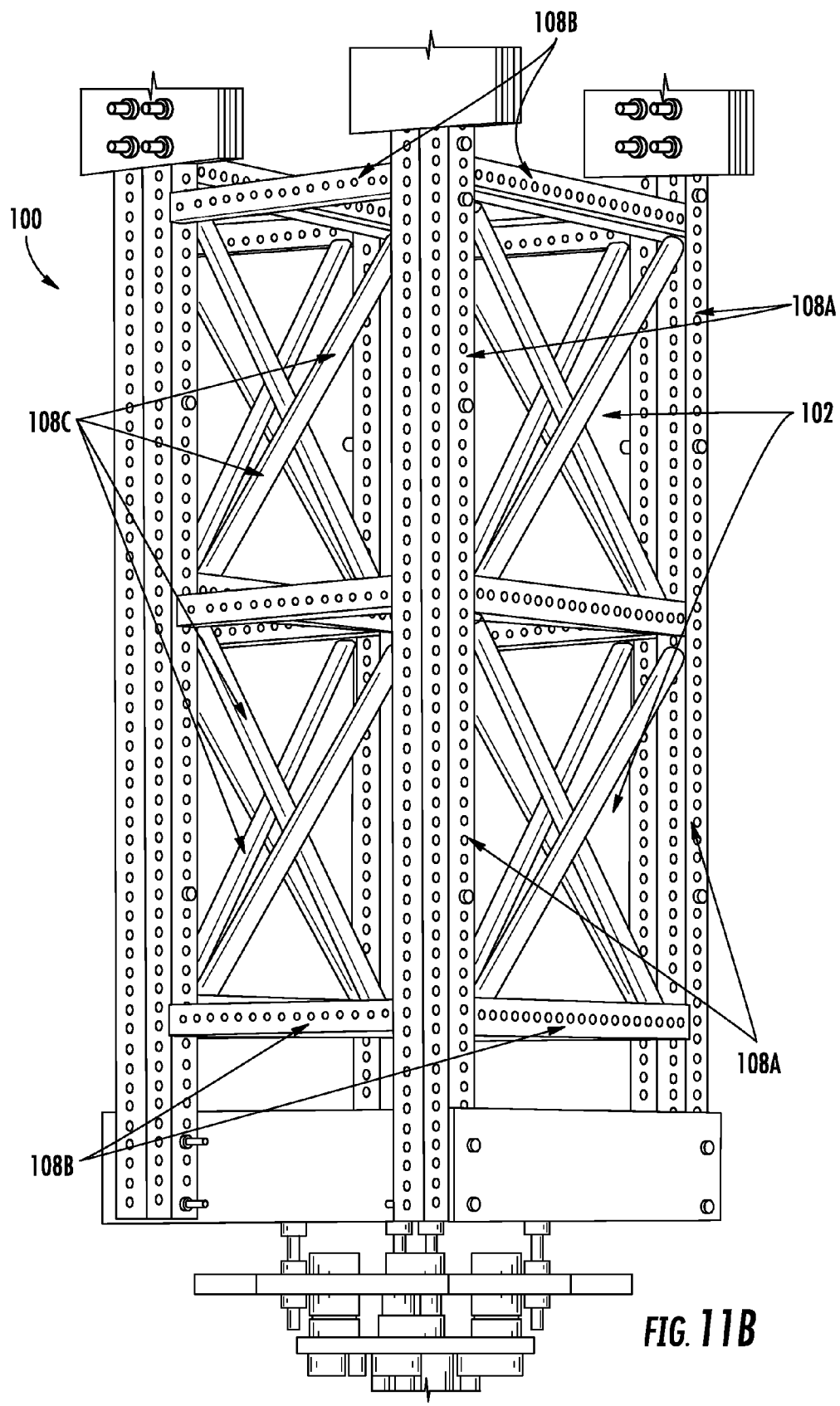

For example, FIGS. 11A and 11B show an embodiment of the disclosed mounting system 100 in which multiple "X" arrangements (i.e., racking arrangements) 102 are disposed adjacent to each other along the length of the system. As with the embodiment described in relation to FIGS. 1 and 2, the "X" arrangements 102 consist of diagonal structural members 108C having first and second ends $108C_1$, $108C_2$, which are positioned to engage adjacent longitudinal and horizontal structural members 108A, 108B to form "X" arrangements between the members 108A, 108B. As can be seen, one end of each diagonal member connects to an end of one pair of horizontal structural members 108B, while another end of each diagonal member 108C connects to another end of the other of the pair of horizontal structural members 108B. The resulting multiple "racking" arrangements shown in FIGS. 11A, 11B provides enhanced racking strength to the mounting structure 100 as compared to systems that include only a single racking arrangement, or no racking arrangement at all.

Thus, the individual components of the disclosed device may be constructed of any of a variety of materials appropriate for the intended application, taking into consideration the strength and rigidity requirements of the application, and the forces applied to the frame system. Steel is one such example of an appropriate material.

While the present invention has been disclosed with reference to certain embodiments, numerous modifications, alterations and changes to the described embodiments are possible without departing from the spirit and scope of the invention, as defined in the appended claims. Accordingly, it is intended that the present invention not be limited to the described embodiments, but that it has the full scope defined by the language of the following claims, and equivalents thereof.

What is claimed is:

1. A medical device mounting system, comprising:
a mounting panel portion comprising a plurality of mounting panels, each of said plurality of mounting panels including a plurality of longitudinal members, a plurality of horizontal members, and a plurality of diagonal members, the plurality of mounting panels arranged such that the mounting panel portion comprises a box beam structure;
a base plate portion connected directly to a first end of each of the longitudinal members, the base plate portion comprising first and second sets of longitudinal members connected to form an egg-crate structure, the base plate portion further comprising a plurality of plate members connected to at least one of said first and second sets of longitudinal members, said plurality of plate members configured to engage a medical device system; and
a structure connection portion connected directly to a second end of each of the longitudinal members, the structure connection portion comprising a plurality of connection sub-sections configured to engage at least one of said longitudinal members of said mounting panels.

2. The medical device mounting system of claim 1, wherein each of said connection sub-sections comprises a plate portion and first and second tubular members connected thereto, each of the first and second tubular members sized and configured to engage first and second longitudinal members of said plurality of longitudinal members of said mounting panel portion.

3. The medical device mounting system of claim 2, wherein the first and second tubular members are received within end portions of the first and second longitudinal members.

4. The medical device mounting system of claim 1, wherein each of said connection sub-sections comprises a plurality of angle clips.

5. The medical device mounting system of claim 1, wherein the plurality of longitudinal members of each of said plurality of mounting panels comprise tubular members having a geometric cross-section.

6. The medical device mounting system of claim 1, wherein the plurality of diagonal members of each of said mounting panels connect to corresponding ones of said plurality longitudinal members and said plurality of horizontal members to form an X-shape therebetween.

7. The medical device mounting system of claim 1, wherein the plurality of diagonal members of each of said mounting panels connect to corresponding ones of said plurality longitudinal members and said plurality of horizontal members to form a first X-shape disposed adjacent to a first end of the mounting panel portion and a second X-shape disposed adjacent to a second end of the mounting panel portion.

8. A medical device mounting system, comprising:
a mounting panel portion comprising a plurality of mounting panels, each of said plurality of mounting panels including a plurality of longitudinally oriented tubular members, a plurality of horizontally oriented tubular members and a plurality of diagonally oriented tubular members, the plurality of mounting panels arranged such that the mounting panel portion comprises a box beam structure;
a base plate portion connected directly to a first end of each of the longitudinally oriented tubular members, the base plate portion comprising a plate member for engaging a medical device system; and
a structure connection portion connected directly to a second end of each of the longitudinally oriented members, the structure connection portion comprising a plurality of connection sub-sections, each of said connection sub-sections configured to engage at least one of said longitudinal members of said mounting panels, each of said connection sub-sections further configured to engage a ceiling support structure for connecting the medical device mounting system to a ceiling structure.

9. The medical device mounting system of claim 8, wherein the base plate portion further comprises a plurality of first and second sets of longitudinal members arranged to form an egg crate structure.

10. The medical device mounting system of claim 8, wherein the plurality of connection sub-sections each including a plurality of angle clips.

11. The medical device mounting system of claim 8, wherein each of said connection sub-sections comprises a plate portion having a plurality of elongated holes, and first and second tubular members, each of the first and second tubular members sized and configured to engage first and second longitudinal members of said plurality of longitudinal members of said mounting panel portion, each of said plurality of elongated holes for receiving a fastener to engage the ceiling structure.

12. The medical device mounting system of claim 8, wherein the first and second tubular members are received within end portions of the first and second longitudinal members.

13. The medical device mounting system of claim 8, wherein the plurality of diagonally oriented tubular members of each of said mounting panels connect to corresponding ones of said plurality longitudinally oriented tubular members and said plurality of horizontally oriented tubular members to form an X-configuration.

14. The medical device mounting system of claim 8, wherein the plurality of diagonally oriented tubular members of each of said mounting panels connect to corresponding ones of said plurality of longitudinally oriented members and said plurality of horizontally oriented members to form a first X-configuration disposed adjacent to a first end of the mounting panel portion and a second X-configuration disposed adjacent to a second end of the mounting panel portion.

15. A medical device mounting system, comprising:
a mounting panel portion comprising a plurality of mounting panels, each of said plurality of mounting panels including a plurality of tubular longitudinal members, a plurality of horizontal members, and a plurality of diagonal members arranged such that the mounting panel portion comprises a box beam structure;
a base plate portion connected directly to a first end of each of the longitudinal members, the base plate portion comprising first and second sets of longitudinal members connected to form an egg-crate structure, and a plurality of plate members configured to engage a medical device system; and
a structure connection portion connected directly to a second end of each of the longitudinal members, the structure connection portion configured to engage at least one of said longitudinal members of said mounting panels.

16. The medical device mounting system of claim 15, wherein the structure connection portion comprises a plurality of connection sub-sections, each of said plurality of connection sub-sections comprising a plate portion and first and second tubular members connected thereto, each of the first and second tubular members sized and configured to engage said mounting panel portion, the plate portion having a plurality of elongated holes for engaging a ceiling structure.

17. The medical device mounting system of claim 16, wherein the first and second tubular members are received within end portions of first and second longitudinal members of said mounting panel portion.

18. The medical device mounting system of claim 15, wherein the plurality of tubular members of each of the mounting panel portions comprise a plurality of longitudinally oriented tubular members, a plurality of horizontally oriented tubular members and a plurality of diagonally oriented tubular members, and wherein the plurality of diagonal members connect to corresponding ones of said plurality longitudinal members and said plurality of horizontal members to form an X-shape therebetween.

19. The medical device mounting system of claim 15, wherein the plurality of diagonally oriented tubular members of each of said mounting panels connect to corresponding ones of said plurality of longitudinally oriented members and said plurality of horizontally oriented members to form a first X-configuration disposed adjacent to a first end of the mounting panel portion and a second X-configuration disposed adjacent to a second end of the mounting panel portion.

\* \* \* \* \*